(12) United States Patent
Higgins et al.

(10) Patent No.: US 7,889,905 B2
(45) Date of Patent: Feb. 15, 2011

(54) FAST 3D-2D IMAGE REGISTRATION METHOD WITH APPLICATION TO CONTINUOUSLY GUIDED ENDOSCOPY

(75) Inventors: William E. Higgins, State College, PA (US); Scott A. Merritt, State College, PA (US); Lav Rai, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 863 days.

(21) Appl. No.: 11/437,230

(22) Filed: May 19, 2006

(65) Prior Publication Data
US 2007/0013710 A1 Jan. 18, 2007

Related U.S. Application Data

(60) Provisional application No. 60/683,588, filed on May 23, 2005.

(51) Int. Cl.
*G06K 9/00* (2006.01)
*G06K 9/32* (2006.01)
*A61B 5/05* (2006.01)

(52) U.S. Cl. ............... 382/130; 382/151; 382/294; 600/424

(58) Field of Classification Search ............ 382/130
See application file for complete search history.

(56) References Cited

U.S. PATENT DOCUMENTS 4,791,934 A  12/1988  Brunnett (Continued)

FOREIGN PATENT DOCUMENTS

KR    20020041577    6/2002

(Continued)

OTHER PUBLICATIONS

Deligianni, F., A. Chung, and G. Yang. "Patient-specific bronchoscope simulation with $pq$-space-based 2D/3D registration." Computer Aided Surgery, vol. 9, No. 5, p. 215-226 (2004).

(Continued)

*Primary Examiner*—David P Rashid
(74) *Attorney, Agent, or Firm*—Gifford, Krass, Sprinkle, Anderson & Citkowski, P.C.

(57) ABSTRACT

A novel framework for fast and continuous registration between two imaging modalities is disclosed. The approach makes it possible to completely determine the rigid transformation between multiple sources at real-time or near real-time frame-rates in order to localize the cameras and register the two sources. A disclosed example includes computing or capturing a set of reference images within a known environment, complete with corresponding depth maps and image gradients. The collection of these images and depth maps constitutes the reference source. The second source is a real-time or near-real time source which may include a live video feed. Given one frame from this video feed, and starting from an initial guess of viewpoint, the real-time video frame is warped to the nearest viewing site of the reference source. An image difference is computed between the warped video frame and the reference image. The viewpoint is updated via a Gauss-Newton parameter update and certain of the steps are repeated for each frame until the viewpoint converges or the next video frame becomes available. The final viewpoint gives an estimate of the relative rotation and translation between the camera at that particular video frame and the reference source. The invention has far-reaching applications, particularly in the field of assisted endoscopy, including bronchoscopy and colonoscopy. Other applications include aerial and ground-based navigation.

17 Claims, 2 Drawing Sheets

U.S. PATENT DOCUMENTS

| | | | |
|---|---|---|---|
| 5,740,802 | A | 4/1998 | Nafis et al. |
| 5,748,767 | A | 5/1998 | Raab |
| 5,765,561 | A | 6/1998 | Chen et al. |
| 5,776,050 | A | 7/1998 | Chen et al. |
| 5,782,762 | A | 7/1998 | Vining |
| 5,792,147 | A | 8/1998 | Evans et al. |
| 5,830,145 | A | 11/1998 | Tenhoff |
| 5,891,034 | A | 4/1999 | Bucholz |
| 5,901,199 | A | 5/1999 | Murphy et al. |
| 5,920,319 | A | 7/1999 | Vining et al. |
| 5,956,418 | A * | 9/1999 | Aiger et al. ............... 382/154 |
| 5,963,612 | A | 10/1999 | Navab |
| 5,963,613 | A | 10/1999 | Navab |
| 5,971,767 | A | 10/1999 | Kaufman et al. |
| 5,999,840 | A | 12/1999 | Grimson et al. |
| 6,006,126 | A | 12/1999 | Cosman |
| 6,016,439 | A | 1/2000 | Acker |
| 6,019,725 | A * | 2/2000 | Vesely et al. ............... 600/447 |
| 6,049,582 | A | 4/2000 | Navab |
| 6,083,162 | A | 7/2000 | Vining |
| 6,190,395 | B1 | 2/2001 | Williams |
| 6,201,543 | B1 | 3/2001 | O'Donnell et al. |
| 6,236,743 | B1 | 5/2001 | Pratt |
| 6,241,657 | B1 | 6/2001 | Chen et al. |
| 6,272,366 | B1 | 8/2001 | Vining |
| 6,311,116 | B1 | 10/2001 | Lee et al. |
| 6,334,847 | B1 | 1/2002 | Fenster et al. |
| 6,343,936 | B1 | 2/2002 | Kaufman et al. |
| 6,351,573 | B1 | 2/2002 | Schneider |
| 6,363,163 | B1 * | 3/2002 | Xu et al. ............... 382/130 |
| 6,366,800 | B1 | 4/2002 | Vining et al. |
| 6,442,417 | B1 | 8/2002 | Shahidi et al. |
| 6,470,207 | B1 * | 10/2002 | Simon et al. ............... 600/426 |
| 6,480,732 | B1 * | 11/2002 | Tanaka et al. ............... 600/425 |
| 6,491,702 | B2 | 12/2002 | Heilbrun et al. |
| 6,514,082 | B2 | 2/2003 | Kaufman et al. |
| 6,535,756 | B1 * | 3/2003 | Simon et al. ............... 600/424 |
| 6,546,279 | B1 | 4/2003 | Bova et al. |
| 6,556,695 | B1 * | 4/2003 | Packer et al. ............... 382/128 |
| 6,593,884 | B1 | 7/2003 | Gilboa et al. |
| 6,674,879 | B1 | 1/2004 | Weisman et al. |
| 6,675,032 | B2 | 1/2004 | Chen et al. |
| 6,694,163 | B1 | 2/2004 | Vining |
| 6,714,668 | B1 | 3/2004 | Kerrien et al. |
| 6,725,080 | B2 * | 4/2004 | Melkent et al. ............... 600/424 |
| 6,771,262 | B2 | 8/2004 | Krishnan |
| 6,785,410 | B2 | 8/2004 | Vining et al. |
| 6,816,607 | B2 * | 11/2004 | O'Donnell et al. ............... 382/131 |
| 6,819,785 | B1 | 11/2004 | Vining et al. |
| 6,859,203 | B2 | 2/2005 | van Muiswinkel et al. |
| 6,909,913 | B2 | 6/2005 | Vining |
| 6,920,347 | B2 | 7/2005 | Simon et al. |
| 6,928,314 | B1 * | 8/2005 | Johnson et al. ............... 600/407 |
| 6,947,584 | B1 | 9/2005 | Avila et al. |
| 6,980,682 | B1 | 12/2005 | Avinash et al. |
| 7,019,745 | B2 | 3/2006 | Goto et al. |
| 7,343,036 | B2 | 3/2008 | Kleen et al. |
| 2002/0057345 | A1 * | 5/2002 | Tamaki et al. ............... 348/207 |
| 2003/0103212 | A1 * | 6/2003 | Westphal et al. ............... 356/479 |
| 2003/0152897 | A1 | 8/2003 | Geiger |
| 2004/0209234 | A1 | 10/2004 | Geiger |
| 2004/0252870 | A1 | 12/2004 | Reeves et al. |
| 2005/0074151 | A1 * | 4/2005 | Chen et al. ............... 382/128 |
| 2005/0078858 | A1 | 4/2005 | Yao et al. |
| 2005/0096526 | A1 | 5/2005 | Reinschke |
| 2005/0182295 | A1 * | 8/2005 | Soper et al. ............... 600/117 |
| 2005/0272999 | A1 | 12/2005 | Guendel |
| 2006/0084860 | A1 | 4/2006 | Geiger et al. |
| 2008/0262297 | A1 * | 10/2008 | Gilboa et al. ............... 600/109 |

FOREIGN PATENT DOCUMENTS

WO    WO-2006076789    7/2006

OTHER PUBLICATIONS

Lee, P.Y. and J.B. Moore. "Pose Estimation via Gauss-Newton-on-manifold." 16th International Symposium on Mathematical Theory of Network and System (MTNS), Leuven, 2004.

Hamadeh, A., S. Lavallee, and P. Cinquin. "Automated 3-Dimensional Computed Tomographic and Fluoroscopic Image Registration." Computer Aided Surgery 1998, vol, 3: p. 11-19.

Roberson, R.E. and P.W. Likins. "A Linearization Tool for Use with Matrix Formalisms of Rotational Dynamics." Archive of Applied Mathematics, vol. 37, No. 6: p. 388-392. Nov. 1969.

Asano, F., Y. Matsuno, T. Matsushita, H. Kondo, Yoshio Saito, A. Seko, and Y. Ishihara. "Transbronchial Diagnosis of a Pulmonary Peripheral Small Lesion Using an Ultrathin Bronchoscope with Virtual Bronchoscopic Navigation." Journal of Bronchology (2002), vol. 9, No. 2, p. 108-111.

Geiger, B., G.M. Weiner, K. Schulze, J. Bilger, P. Krebs, K. Wolf, T.Albrecht. "Virtual Bronchoscopy Guidance System for Transbronchial Needle Aspiration." Proceedings of SPIE vol. 5746 (2005).

Grimson, W.E.L., G.J. Ettinger, S.J. White, T. Lozano-Perez, W.M. Wells III, and R. Kikinis. "An Automatic Registration Method for Frameless Stereotaxy, Image Guided Surgery, and Enhanced Reality Visualization." IEEE Transactions on Medical Imaging, Apr. 1996, vol. 15, No. 2, p. 129-140.

Helferty, J.P., A.J. Sherbondy, A.P. Kiraly, and W.E. Higgins. "Computer-based System for the Virtual Endoscopic Guidance of Bronchoscopy." (believed to have been offered for sale, publicly used, and/or published prior to the filing date of this application).

Hopper, K.D., T.A. Lucas, K. Gleeson, J.L. Stauffer, R. Bascom, D. T. Mauger, R. Mahraj. "Transbronchial Biopsy with Virtual CT Bronchoscopy and Nodal Highlighting." Radiology Nov. 2001, vol. 221, No. 2, p. 531-536.

Maurer, C.R., J.M. Fitzpatrick, M.Y. Wang, R.L. Galloway, Jr., R.J. Maciunas, and G.S. Allen. "Registration of Head Volume Images Using Implantable Fiducial Markers." IEEE Transactions on Medical Imaging, Aug. 1997, vol. 16, No. 4, p. 447-462.

McAdams, H.P., P.C. Goodman, and P. Kussin. "Virtual Bronchoscopy for Directing Transbronchial Needle Aspiration of Hilar and Mediastinal Lymph Nodes: A Pilot Study." AJR May 1998, vol. 170, p. 1361-1364.

Merritt, S.A., L. Rai, and W.E. Higgins. "Real-Time CT-Video Registration for Continuous Endoscopic Guidance." (believed to have been offered for sale, publicly used, and/or published prior to the filing date of this application).

Mori, K., T. Enjoji, D. Deguchi, T. Kitasaka, Y. Suenaga, J. Toriwaki, H. Takabatake, and H. Natori. "New image similarity measures for bronchoscope tracking based on image registration between virtual and real bronchoscopic images." (believed to have been offered for sale, publicly used, and/or published prior to the filing date of this application).

Rai, L., S.A. Merritt, and W.E. Higgins. "Real-time Image-based Guidance Method for Lung-Cancer Assessment." (believed to have been offered for sale, publicly used, and/or published prior to the filing date of this application).

Sato, Y., M. Nakamoto, Y. Tamaki, T. Sasama, I. Sakita, Y. Nakajima, M. Monden, and S. Tamura. "Image Guidance of Breast Cancer Surgery Using 3-D Ultrasound Images and Augmented Reality Visualization." IEEE Transactions on Medical Imaging, Oct. 1998, vol. 17, No. 5, p. 681-693.

Schwarz, Y., A.C. Mehta, A. Ernst, F. Herth, A. Engel, D. Besser, and H. D. Becker. "Electromagnetic Navigation during Flexible Bronchoscopy." Respiration 2003, vol. 70, p. 516-522.

Shinagawa, N., K. Yamazaki, Y. Onodera, K. Miyasaka, E. Kikuchi, H. Dosaka-Akita, and M. Nishimura. "CT-Guided Transbronchial Biopsy Using an Ultrathin Bronchoscope with Virtual Bronchoscopic Navigation." Chest, Mar. 2004, vol. 25, p. 1138-1143.

Shoji, H., K. Mori, J. Sugiyama, Y. Suenaga, J. Toriwaki, H. Takabatake, and H. Natori. "Camera motion tracking of real endoscope by using virtual endoscopy system and texture information." Proceedings of SPIE vol. 4321, p. 122-133 (2001).

Stefansic, J.D., A.J. Herline, Y. Shyr, W.C. Chapman, J.M. Fitzpatrick, B.M. Dawant, and R.L. Galloway, Jr. "Registration of Physical Space to Laparoscopic Image Space for Use in Minimally Invasive Hepatic Surgery." IEEE Transactions on Medical Imaging, Oct. 2000, vol. 19, No. 10, p. 1012-1023.

Turcza, P. and M. Duplaga. "Navigation Systems Based on Registration of Endoscopic and CT-derived Virtual Images for Bronchofiberoscopic Procedures." Studies in Health Technology and Informatics, vol. 105, p. 253-263 (2004).

White, C.S., E.A. Weiner, P. Patel, and E.J. Britt. "Transbronchial Needle Aspiration: Guidance with CT Fluoroscopy." Chest 2000, vol. 118, No. 6, p. 1630-1638.

Higgins, W., W.J.T. Spyra, R.A. Karwoski, and E.L. Ritman. "System for Analyzing High-Resolution Three-Dimensional Coronary Angiograms." IEEE Transactions on Medical Imaging, Jun. 1996, vol. 15, No. 3, p. 377-385.

Brady, M.L., W.E. Higgins, K. Ramaswamy. "Interactive navigation inside 3D radiological images." IEEE 1995, p. 33-40.

Higgins, W.E. and K. Ramaswamy. "Toward dynamic visualization for endoscopy simulation." IEEE 1994, p. 700-701.

Bricault, I., G. Ferretti, and P. Cinquin. "Registration of Real and CT-Derived Virtual Bronchoscopic Images to Assist Transbronchial Biopsy." IEEE Transactions on Medical Imaging, Oct. 1998, vol. 17, No. 5, p. 703-714.

Sherbondy, A.J., A.P. Kiraly, A.L. Austin, J.P. Helferty, S. Wan, J.Z. Turlington, T. Yang, C. Zhang, E.A. Hoffman, and G. McLennan. "Virtual Bronchoscopic approach for combining 3D CT and Endoscopic Video." Proceedings of SPIE 2000, vol. 3978, No. 104.

Helferty, J.P., A.J. Sherbondy, A.P. Kiraly, J.Z. Turlington, E.A. Hoffman, G. McLennan, W.E. Higgins. "Experiments in virtual-endoscopic guidance of bronchoscopy." Proceedings of SPIE 2001, vol. 4321, No. 111.

Helferty, J.P. and W.E. Higgins. "Combined endscopic video tracking and virtual 3D CT registration for surgical guidance." Proceedings of the 2002 International Conference on Image Processing, vol. 2, pp. 961-964.

Higgins, W.E., J.P. Helferty, and D.R. Padfield. "Integrated bronchoscopic video tracking and 3D CT registration for virtual bronchoscopy." Proceedings of SPIE 2003, vol. 5031, No. 80.

Kiraly, A.P., J.P. Helferty, E.A. Hoffman, G. McLennan, W.E. Higgins. "Three-dimensional path planning for virtual bronchoscopy." IEEE Transactions on Medical Imaging 2004, vol. 23, No. 11, pp. 1365-1379.

Helferty, J.P., E.A. Hoffman, G. McLennan, W.E. Higgins. "CT-video registration accuracy for virtual guidance of bronchoscopy." Proceedings of SPIE 2004, vol. 5369, pp. 150-164.

Higgins, W.E., L. Rai, S.A. Merritt, K. Lu, N. T. Linger, and K.C. Yu. "3D image fusion and guidance for computer-assisted bronchoscopy." Proceedings of SPIE 2005, vol. 6016.

Asano, F., Y Matsuno, N. Shinagawa, K. Yamazaki, T. Suzuki, T. Ishida, and H. Moriya. "A Virtual Bronchoscopic Navigation System for Pulmonary Peripheral Lesions." Chest 2006, vol. 130, No. 2, pp. 559-566.

Kukuk, M. "Modeling the Internal and External Constraints of a Flexible Endoscope for Calculating its Workspace: Application in Transbronchial Needle Aspiration Guidance." Proceedings of SPIE 2002, vol. 4681, pp. 539-550.

Gibbs, J.D. and W.E. Higgins. "3D Path Planning and Extension for Endoscopic Guidance." Proceedings of SPIE 2007, vol. 6509.

Mori, K., S. Ema, T. Kitasaka, Y. Mekada, I. Ide, H. Murase, Y. Suenaga, H. Takabatake, M. Mori, and H. Natori. "Automated Nomenclature of Bronchial Branches Extracted from CT Images and Its Application to Biopsy Path Planning in Virtual Bronchoscopy." Medical Image Computing and Computer-Assisted Intervention 2005, Lecture Notes in Computer Science 3750, pp. 854-861.

Kiraly, et al., 3D human airway segmentation for virtual bronchoscopy, *Proceedings of SPIE*, 4683: 16-29, 2002.

Lucas, et al., An iterative image registration technique with an application to stereo vision, *Proceedings of the 7th International Joint Conference on Artificial Intelligence (IJCAI '81)*, Apr. 1981, pp. 674-679.

Minami, et al., Interbronchoscopist variability in the diagnosis of lung cancer by flexible bronchoscopy, *Chest*, 105:1658-1662, 1994.

Okatani, et al., Shape reconstruction from an endoscope image by shape from shading technique for a point light source at the projection center, *Computer Vision and Image Understanding*, 66:119-131, 1997.

Shum, et al., Systems and experiment paper: construction of panoramic image mosaics with global and local alignment, *International Journal of Computer Vision*, 36(2): 101-130, 2000.

Shum, et al, Panoramic image mosaics, Microsoft Research, Technical Report MSR-TR-97-23, 1997.

Swift, et al., Automatic axis generation for virtual bronchoscopic assessment of major airway obstructions, Computerized Medical Imaging and Graphics, 26: 103-118, 2002.

Asano, et al., Transbronchial diagnosis of a pulmonary peripheral small lesion using an ultrthin bronchoschope with virtual bronchoscopic navigation, Journal of Bronchology, 9: 108-11, 2002.

Helferty, et al., Technique for registering 3D virtual CT images to endoscopic video, IEEE Image Processing, 893-896, 2001.

Baker, et al., Equivalence and efficiency of image alignment algorithms, Proceedings of the 2001 Conference on Computer Vision and Pattern Recognition, 1090-1097.

Bricault, et al., Registration of real and CT-derived virtual bronchoscopic images to assist transbronchial biopsy, IEEE Transactions of Medical Imaging, 17(5):703-714, 1998.

Deguchi, et al., Camera motion tracking of real bronchoscope using epipolar geometry analysis and CT derived bronchoscopic images, Proceedings of SPIE, 4683: 30-41, 2002.

Haralick, et al., Analysis and solutions of the three point perspective pose estimation problem, Proceedings Computer vision and pattern recognition, IEEE Computer Society Conference, 592-598, 1991.

Harris, et al., A combined corner and edge detector, Proceedings of the Fourth Alvey Vision Conference, 147-151, 1988.

Horaud, et al., A analytic solution for the perspective 4-point problem, Computer Vision, Graphics, and Image Processing, 47:33-44, 1989.

Fischler, et al., Random sample consensus: a paradigm for model fitting with application to image analysis and automated cartography, Communications of the ACM, 24(6): 381-395, 1981.

Zuliani, et al., A mathematical comparison of point detectors, Proceedings of the 2004 IEEE Computer Society Conference on Computer Vision and Pattern Recognition Workshops.

Ansar, et al., Linear pose estimation from points or lines, IEEE Transactions on Pattern Analysis and Machine Intelligence, 25(5):578:589, 2003.

Mori, et al., A method for tracking the camera motion of real endoscope by epipolar geometry analysis and virtual endoscopy system, Lecture Notes in Computer Science, 2208: 1-8, 2001.

Shi, et al., Good features to track, IEEE Conference on Computer Vision and Pattern Recognition, 593-600, 1994.

Triggs, B., Detecting keypoints with stable position, orientation, and scale under illumination changes, Lecture Notes on Computer Science, 3024: 100-113, 2004.

Quan, et al., Linear N-point camera pose determination, IEEE Transactions on Pattern Analysis and Machine Intelligence, 21(8): 774-780, 1999.

Haralick, et al., Pose estimation from corresponding point data, IEEE Transaction on Systems, Man, and Cybernetics, 19(6): 1426-1446, 1989.

Lowe, D., Fitting parameterized three-dimensional models to images, IEEE Transaction on Pattern Analysis and Machine Intelligence, 13(5):441-450, 1991.

Hager, et al., Fast and globally convergent pose estimation from video images, IEEE Transactions on Pattern Analysis and Machine Intelligence, 22(6):610-622, 2000.

Hartley, et al., Multiple View Geometry in Computer Vision, Cambridge University Press, ISBN:0521623049, pp. 238, 239, 281, 2000.

Higgins, et al., Integrated bronchoscopic video tracking and 3D CT registration for virtual bronchoscopy, Medical Imaging 2003: Physiology and Function: Methods, Systems, and Applications.

Mori, et al., New image similarity measures for bronchoscope tracking based on image registration between virtual and real bronchoscopic images, Medical Imaging 2004: Physiology, Function, and Structure from Medical Images, 165-176.

Shoji, et al., Camera motion tracking of real endoscope by using virtual endoscopy system and texture information, Medical Imaging 2001: Physiology and function from Multidimensional Images.

Helferty, et al., Combined endoscopic video tracking and virtual 3D CT registration for surgical guidance, IEEE International Conference on Image Processing, 2002.

Helferty, J., Image-guided endoscopy and its application to pulmonary medicine, A Thesis in Electrical Engineering, The Pennsylvania State University, 2002.

* cited by examiner

FAST 3D-2D IMAGE REGISTRATION METHOD WITH APPLICATION TO CONTINUOUSLY GUIDED ENDOSCOPY

REFERENCE TO RELATED APPLICATION

This application claims priority to U.S. Provisional Patent Application Ser. No. 60/683,588, filed May 23, 2005, the entire content of which is incorporated herein by reference.

STATEMENT OF GOVERNMENT SPONSORSHIP

This invention was made with government support under Grant No. R01 CA074325, awarded by the National Institutes of Health. The Government has certain rights in the invention.

FIELD OF THE INVENTION

This invention relates generally to image correlation and, in particular, to a fast image registration method applicable to guided endoscopy and other fields.

BACKGROUND OF THE INVENTION

Registration and alignment of images taken by cameras at different spatial locations and orientations within the same environment is a task which is vital to many applications in computer vision and medical imaging. For example, registration between images taken by a mobile camera and those from a fixed surveillance camera can assist in robot navigation. Other applications include the ability to construct image mosaics and panoramas, high dynamic range images, or super-resolution images, or the fusion of information between the two sources.

However, because the structure of a scene is inherently lost by the 2D imaging of a 3D scene, only partial registration information can typically be recovered. In many applications, depth maps can be generated or estimated to accompany the images in order to reintroduce the structure to the registration problem.

Most currently available 2D alignment algorithms use a gradient descent approach which relies on three things: a parameterization of the spatial relationship between two images (e.g., the 2D rotation and translation between two 2D images), the ability to visualize these images under any value of the parameters (e.g., viewing a 2D reference image rotated by 30 degrees), and a cost function with associated image gradient information which allows an estimate of the parameter updates to be calculated. Among the most straightforward and earliest of these algorithms is the Lucas-Kanade algorithm, which casts image alignment as a Gauss-Newton minimization problem [5]. A subsequent refinement to this algorithm includes the inverse compositional alignment algorithm which greatly speeds the computation of the parameter update by recasting the problem, allowing all gradient and Hessian information to be calculated one time instead of every iteration [6]. Several other improvements have centered around the choice of parameters and the corresponding image warps these parameterizations induce. For example, images obtained from two identical cameras observing the same scene from a different location can be approximately related by an affine transformation or an 8-parameter homography [7].

The main problem with these types of parameterizations is that they do not truly capture the physically relevant parameters of the system, and, in the case of the homography, can lead to overfitting of the image. A more recent choice of parameters attempts to match two images obtained from a camera that can have arbitrary 3D rotations around its focal point [8]. This algorithm succeeds in extracting the physically relevant parameters (rotation angles about the focal point). However, while it is able to handle small translations, it cannot handle general translation and treats it as a source of error.

Little has been done to tackle the problem of registration of two images generated by cameras related by a general rigid transformation (i.e., 3D rotation and translation). The main reason for this is that the accurate visualization of a reference image as seen from a different camera location ideally requires that the depth map associated with that image be known—something which is not generally true. In certain situations, such as a robot operating in a known man-made environment, or during bronchoscopy where 3D scans are typically performed before the procedure, this information is known. Indeed, even in situations where the depth map is unknown, it can often be estimated from the images themselves.

An example of this is the aforementioned shape-from-shading problem in bronchoscopy guidance [9]. Current practice requires a physician to guide a bronchoscope from the trachea to some predetermined location in the airway tree with little more than a 3D mental image of the airway structure, which must be constructed based on the physician's interpretation of a set of computed tomography (CT) films. This complex task can often result in the physician getting lost within the airway during navigation [1]. Such navigation errors result in missed diagnoses, or cause undue stress to the patient as the physician may take multiple biopsies at incorrect locations, or the physician may need to spend extra time returning to known locations in order to reorient themselves.

In order to alleviate this problem and increase the success rate of bronchoscopic biopsy, thereby improving patient care, some method of locating the camera within the airway tree must be employed. Fluoroscopy can provide intraoperative views which can help determine the location of the endoscope. However, as the images created are 2D projections of the 3D airways, they can only give limited information of the endoscope position. Additionally, fluoroscopy is not always available and comes with the added cost of an increased radiation dose to the patient.

A few techniques also exist that determine the bronchoscope's location by attempting to match the bronchoscope's video to the preoperative CT data. One method uses shape-from-shading, as in [2], to estimate 3D surfaces from the bronchoscope images in order to do 3D-to-3D alignment of the CT airway surface. This method requires many assumptions to be made regarding the lighting model and the airway surface properties and results in large surface errors when these assumptions are violated. A second method of doing this is by iteratively rendering virtual images from the CT data and attempting to match these to the real bronchoscopic video using mutual information [3] or image difference [4].

While these methods can register the video to the CT with varying degrees of success, all operate very slowly and only involve single-frame registration—none of them are fast enough to provide continuous registration between the real video and the CT volume. They rely on optimization methods which make no use of either the gradient information nor the known depth of the CT-derived images, and thus require very computationally intensive searches of a parameter space.

SUMMARY OF THE INVENTION

This invention resides in a novel framework for fast and continuous registration between two imaging modalities. A method of registering an image according to the invention comprises the steps of providing a set of one or more reference images with depth maps, and registering the image to at least one of the reference images of the set using the depth map for that reference image. The image and the reference set may both be real, virtual, or one real with the other virtual. The set of reference images may endoscopic, derived from a bronchoscope, colonoscope, laparoscope or other instrument. The registration preferably occurs in real-time or near real-time, and one or more of the images in the set of reference images can be updated before, during, or after registration.

According to a robust implementation, the set of reference images represents viewpoints with depth maps and image gradients, and the image to be registered is derived from a video feed having a plurality of consecutive frames. The method includes the steps of:

a) warping a frame of the video to the nearest viewpoint of the reference source;
b) computing an image difference between the warped video frame and the reference image;
c) updating the viewpoint using a Gauss-Newton parameter update; and
d) repeating steps a) through c) for each frame until the viewpoint converges or the next video frame becomes available.

The invention makes it possible to completely determine the rigid transformation between multiple sources at real-time or near real-time frame-rates in order to register the two sources. A disclosed embodiment involving guided bronchoscopy includes the following steps:

1. In the off-line phase, a set of reference images is computed or captured within a known environment, complete with corresponding depth maps and image gradients. The collection of these images and depth maps constitutes the reference source.
2. The second source is a real-time source from a live video feed. Given one frame from this video feed, and starting from an initial guess of viewpoint, the real-time video frame is warped to the nearest viewing site of the reference source.
3. An image difference is computed between the warped video frame and the reference image.
4. The viewpoint is updated via a Gauss-Newton parameter update.
5. Steps 2-4 are repeated for each frame until the viewpoint converges or the next video frame becomes available. The final viewpoint gives an estimate of the relative rotation and translation between the camera at that particular video frame and the reference source.

The invention has far-reaching applications, particularly in the field of assisted endoscopy, including bronchoscopy and colonoscopy. Other applications include aerial and ground-based navigation.

BRIEF DESCRIPTION OF THE DRAWINGS

FIG. 2A shows a real video frame, FIG. 2B shows a warped real image at initial viewpoint, FIG. 2C shows edges from final reference image overlaid, FIG. 2D shows a reference virtual image corresponding to final registration, FIG. 2E shows a warped real image at final viewpoint, and FIG. 2F shows edges of corresponding virtual image overlaid; FIG. 3A shows a real image, FIG. 3B shows a reference image, and FIG. 3C shows a warped real image.

DETAILED DESCRIPTION OF THE INVENTION

Figure 1:
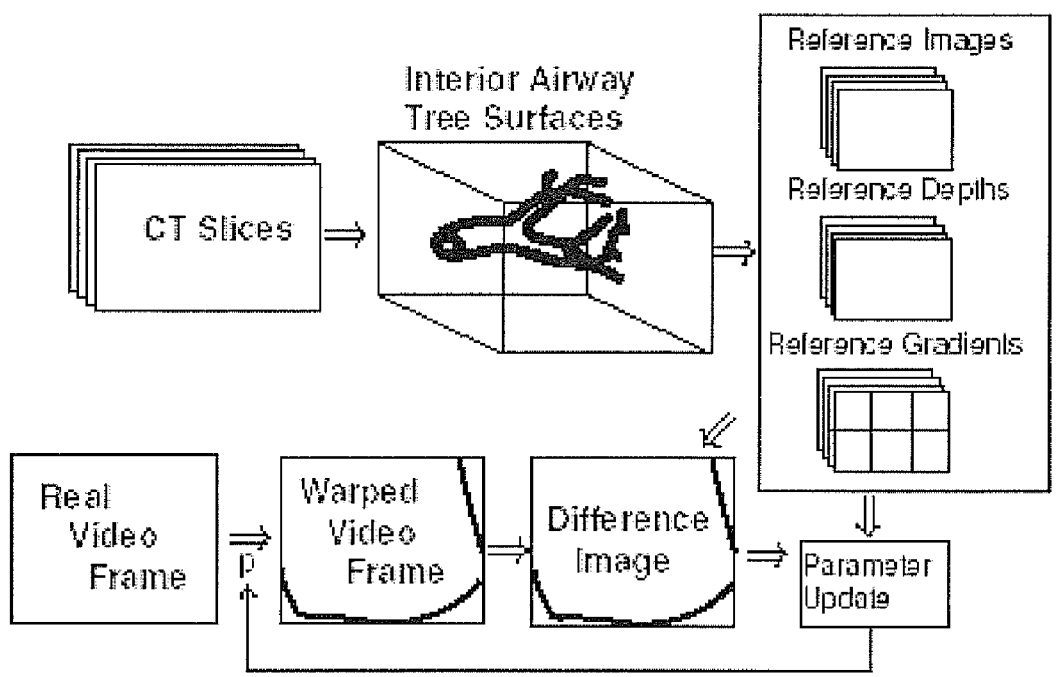
FIG. 1 shows a block diagram of registration algorithm for guided bronchoscopy.

Broadly, this invention is a 2D image alignment algorithm which is augmented to three dimensions by introducing the depth maps of the images. The method provides an ideal way to extend the existing matching framework to handle general 3D camera motion, allowing one to directly solve for the extrinsic parameters of the camera and localize it within its environment.

For the purpose of explaining the method in a very concrete fashion, discussion shall focus on a situation similar to that used in guided bronchoscopy. In a typical bronchoscopic procedure, a CT scan is initially performed and can subsequently be processed to extract the airway tree surfaces. The interior of the hollow airway tree constitutes the known environment. During bronchoscopy, the bronchoscope is inserted into the airways and a camera mounted on the tip transmits in real-time a sequence of real bronchoscopic (RB) video images. Assuming that the calibration parameters of the endoscope are known, virtual bronchoscopic (VB) images (endoluminal renderings) can be rendered at arbitrary viewpoints within the airway tree. It is also clear that the depths corresponding to each pixel of the VB image can be immediately calculated and form a virtual depth map (VDM).

The problem is that we have a fixed real-time RB image from an unknown location within the interior of an airway, but we also have a known VB source with known location and 3D information that enables us to create manifestations of the same hollow airway structure from arbitrary viewpoint. Given the above setup, the goal is to locate the source of the RB image by attempting to find the best match between that fixed RB image and any possible VB endoluminal rendering. A fairly straightforward approach to accomplish this is by employing a Gauss-Newton gradient descent algorithm that attempts to minimize a difference measure between the RB image and the VB image with respect to the viewing parameters (i.e., viewpoint) of the virtual image. The method for doing this is similar to the Lucas-Kanade image alignment algorithm [5].

The objective function used in [5, 6] is the sum squared difference (SSD) between the pixel intensities of the two images, although weighted SSD is equally viable, and weighted or unweighted normalized cross-correlation (CC) can be used if some additional weak assumptions are made. Using the SSD, the objective function can thus be written as $$E = \sum_{u,v} [I_v(u, v; p + \Delta p) - I_r(u, v)]^2 \quad (1)$$

where p is the vector of viewing parameters, $I_v(u, v; p+\Delta p)$ is the virtual VB image rendered from the viewpoint $p+\Delta p$, u and v are the row and column indices, and $I_r$ is the real RB image. Following the procedure of [5], it is shown that that the Gauss-Newton parameter update $\Delta p$ can be found as $$\Delta p = H^{-1} \sum_{u,v} \left[\frac{\partial I}{\partial p}\right][I_v(u, v; p) - I_r(u, v)] \quad (2)$$

where the Hessian H is approximated per Gauss-Newton as $$H = \sum_{u,v} \left[\frac{\partial I_v}{\partial p}\right]^T_{u,v;p} \left[\frac{\partial I_v}{\partial p}\right]_{u,v;p} \quad (3)$$

where $$\left[\frac{\partial I_v}{\partial p}\right]_{(u,v;p)}$$

is a vector that gives the change in the intensity of a pixel (u, v) in a VB image Iv rendered at viewpoint p with respect to each of the components of the parameter vector $\Delta p$.

$$\left[\frac{\partial I_v}{\partial p}\right]_p$$

can also be interpreted as a vector of steepest descent images, where each component of the vector is actually an image that describes the variation of the image intensities with respect a component of the parameter vector. Because the steepest descent images $$\left[\frac{\partial I_u}{\partial p}\right]_p$$

change at every viewpoint p, they, and the Hessian must be recomputed every iteration, leading to a very computationally costly algorithm.

To speed up the iteration, the inverse compositional algorithm was proposed [6]. Under this strategy, instead of moving the virtual viewpoint towards the real viewpoint using the parameter update, we instead move the real viewpoint toward the virtual viewpoint using the inverse of the parameter update. Since the computer obviously has no control over the location of the bronchoscope tip, this may seem to be an unfeasible strategy. However, using a depth-based warping, the RB image can be warped to simulate its appearance from other viewpoints. This strategy results in comparing a warped version of the real image to a stationary virtual image. Under this formulation, the objective function we seek to minimize is:

$$E = \sum_{u,v} [I_v(u, v; \Delta p) - I_r(W(u, v, Z_r; p))]^2 \quad (4)$$

The warping function W (•) warps the image coordinates of the RB image $I_r$ and hence warps the image itself. It is important also to note that the warp in this case is dependent on the depth map of the real image $Z_r$. Solving for the Gauss-Newton parameter update associated with 4 yields $$\Delta p = H^{-1}|_{\vec{p}=\vec{0}} \sum_{u,v} \left[\frac{\partial I}{\partial p}\right]_{u,v;\vec{0}} [I_r(W(u, v, Z_r; p)) - I_v(u, v)] \quad (5)$$

While this may seem to add unnecessary complexity and error to the problem, it actually serves to greatly speed the iteration and has the additional side benefit of eliminating the need to render arbitrary viewpoints on the fly if you instead have a collection of pre-rendered (or pre-captured) images and corresponding depth maps. The reason for this significant increase in speed is that the VB image and VB image gradients are always evaluated at p=0, the reference viewing site, and as such allows all of the following operations to be pre-computed before iteration begins:

1. The known environment is sampled as a set of viewing sites.
2. Virtual images $I_v$ are pre-rendered at each viewing site.
3. Virtual depth maps $Z_v$ are computed at each site.
4. Steepest descent images $$\frac{\partial I_v}{\partial p}$$

are computed with respect to each of the viewing parameters in vector p.

5. The inverse Hessian $H^{-1}$ is Gauss-Newton estimated from the steepest descent images $$\frac{\partial I_v}{\partial p}$$

via equation (14).

The iterative portion of the algorithm may then be carried out in the following steps:

1. Warp the real image from pose p to the nearest reference site.
2. Compute the error image: $I_r(W(u,v, Z_r;p))-I_v(u, v;0)$.
3. Compute the parameter update $\Delta p$ via equation (5).
4. Find the new values of p by incrementing the old parameters by the inverse of the update $(\Delta p)^{-1}$.

These steps are illustrated in FIG. 1. Ignoring the warp function, all the equations presented thus far are general and can apply equally well to 2D transformations, such as affine or homography, or 3D rotations. The focus is now narrowed, however, to the full 3D motion case with our choice of coordinate system and parameters. One may realize from inspection of the warps in (4) that the problem is defined in terms of several local coordinate systems as each reference view is defined to be at p=$0_1$, yielding a different coordinate system for each viewing site used. It is, however, a trivial matter to relate each of these coordinate systems to a global coordinate frame in order to perform parameter conversions between frames. Therefore, given a camera pose with respect to the global camera frame, we can define our parameter vector as $$p=[\theta_r, \theta_p, \theta_y, t_x, t_y, t_x]^T \quad (6)$$

with three Euler rotation angles and three translations with respect to the nearest reference view.

With this parameterization, the warping $W(u,v,Z;p)$ is governed by the matrix equation $$\begin{bmatrix} \frac{u'Z'}{f} \\ \frac{v'Z'}{f} \\ Z' \end{bmatrix} = R \begin{bmatrix} \frac{uZ}{f} \\ \frac{vZ}{f} \\ Z \end{bmatrix} + \begin{bmatrix} t_x \\ t_y \\ t_z \end{bmatrix} \quad (7)$$

where R is the rotation matrix defined by the Euler angles $(\theta_r, \theta_p, \theta_y)$, u and v are the columns and rows of the image, f is the focal length, and Z is the entry on the depth map Z corresponding to the point $(u,v)$. Here $(u',v')$ gives the warped image coordinate of interest, and Z' gives the warped depth corresponding to that point. Note that in the problem statement, we assume only that the virtual depth map $Z_v$ is known. However, when using the inverse compositional algorithm, the warp is applied to the real image $I_r$ and the real depth map $Z_r$ must first be calculated by warping the virtual depth map $Z_v$ to the current estimated pose of the real camera via p. This can also be performed using (7) and then interpolating the resulting warped depth map onto the coordinate system of the real image. In doing so, we are implicitly assuming that our estimate of p is relatively close to its actual value. If this is not the case, the parameter error can lead to large errors in the real depth map $Z_r$, and therefore large errors in the image warping. Under such circumstances, the forward gradient descent method governed by (1-2) may be better suited to the problem.

In order to apply the warping function, at each pixel coordinate $(u,v)$, with intensity $I(u,v)$ and depth $Z(u,v)$, a new coordinate $(u',v')$ and depth $Z'(u',v')$ are found via (7). The original intensities and depths may then be mapped onto the new image array $I(u',v')$. Some special care must be taken when performing the warping. Firstly, the image difference in (4) requires that the coordinate locations be the same for both images. The resultant array must therefore be interpolated onto the same coordinate grid as the original arrays. Because of this interpolation, and because the depth-based warping may result in occlusion, it can be difficult to choose the proper intensity corresponding to an output pixel. This can be mitigated somewhat if the intensities corresponding to larger depths are discarded when they overlap with those of smaller depths.

Finally, we turn to the calculation of the steepest-descent images $$\frac{\partial I}{\partial p}.$$

There are several ways to generate the steepest descent images. They may be generated numerically by taking the difference of the reference images warped to small positive and negative values of each parameter. They may also be generated analytically by expanding the derivative via the chain rule:

$$\frac{\partial I}{\partial p} = [\nabla_u I \quad \nabla_v I] J_p \quad (8)$$

where $\nabla_u I$ and $\nabla_v I$ are the image gradients with respect to the rows and columns of the image, and $J_p$ is the Jacobian of the warped coordinates with respect to p and thus can be found by differentiating u' and v' from (7) with respect to each of the warp parameters and evaluating it at a particular current value of p. In the case of the inverse compositional algorithm, the image derivatives are always evaluated at $p=0$ and thus the Jacobian is constant for each reference viewing site:

$$J_p = \begin{bmatrix} -v & -\frac{uv}{f} & -f - \frac{u^2}{f} & \frac{f}{Z} & 0 & -\frac{u}{Z} \\ -u & -f - \frac{v^2}{f} & -\frac{vu}{f} & 0 & \frac{f}{Z} & -\frac{v}{Z} \end{bmatrix} \quad (9)$$

We now have all the necessary information to calculate the iterated parameter update $\Delta p$. The final step is to invert this update, and compose it with the current estimate of p. The Euler angles can be found from the rotation matrix resulting from $$R' = R R_d^T \quad (10)$$

where $R_d$ is the incremental rotation matrix associated with the rotation angles in $\Delta p$. The updated translations can be found from $$\begin{pmatrix} t_x^d \\ t_y^d \\ t_z^d \end{pmatrix} = \begin{pmatrix} t_x \\ t_y \\ t_z \end{pmatrix} - R R_d^T \begin{pmatrix} \Delta t_x \\ \Delta t_y \\ \Delta t_z \end{pmatrix} \quad (11)$$

where $\Delta t_i$ are the translation elements of the parameter update $\Delta p$.

In order to improve the performance when applying the above approach, several optimizing techniques are used. Operations performed on full-resolution images can be very computationally intensive. Therefore, a resolution pyramid is used wherein all images, depth maps, and gradients are downsampled, preferably by a factor of 4, at each level. As we are not particularly concerned with computation time regarding the precomputed virtual views and gradients, and most video capture hardware provides real-time hardware subsampling for the real image, the computational cost of this subsampling is inconsequential and provides much quicker iteration times.

When implementing the above registration algorithm using pyramid decomposition, the algorithm is begun at the lowest resolution level of the pyramid (experimental results in this paper were performed starting at level 3; i.e., a factor of 64 reduction in resolution) and run until a reasonable stopping criteria was met before proceeding to a higher resolution level. This pyramidal approach not only speeds computation, it also serves to prevent convergence to local optima, because only the largest features are present in the highly subsampled images, while sharper features are introduced in higher resolution levels to aid in fine adjustment.

A second optimization that is used in practice is the use of the weighted normalized cross-correlation objective function $$E = -\sum_{u,v} w_{u,v} \begin{bmatrix} \dfrac{I_v(W(u, v, Z; \Delta p)) - \mu_0}{\sigma_v} \\ \dfrac{I_r(W(u, v, Z; p)) - \mu_r}{\sigma_r} \end{bmatrix} \quad (12)$$

that allows images of different mean intensities and intensity ranges to be compared and also allows weighting of individual pixel values. It should be noted that in order to use this objective function under the inverse compositional algorithm, the weights must be constant and they must be chosen prior to the computation of the steepest descent images (i.e. they must be based off features of the virtual images). Taking advantage of the equivalence of normalized SSD and normalized cross-correlation, the update can be found as:

$$\Delta_p = H^{-1} \Bigg|_{p=0} \sum_{u,v} w_{u,v} \left[\dfrac{\partial I}{\partial p}\right]^T_{p=0} [\bar{I}_r(W(u, v, Z; p)) - \bar{I}_v(u, v)] \quad (13)$$

where the Hessian in this case is $$H = \sum_{u,v} w_{u,v} \left[\dfrac{\partial I}{\partial p}\right]^T \left[\dfrac{\partial I}{\partial p}\right], \quad (14)$$

$$\left[\dfrac{\partial I}{\partial p}\right]$$

is the set of mean-subtracted steepest descent images divided by the variance of the virtual image $I_v$, and $\bar{I}_r i$ are the normalized images.

Examples

To validate the algorithm, sample results for the virtual-to-real and virtual-to-virtual registration cases are given. In both of the cases outlined below, the virtual environment is a CT chest scan of a human patient designated h005. The airway surfaces were automatically generated using the methods of Kiraly et al. [10]. Airway centerlines were extracted using the methods of Swift et al. and the virtual viewing sites were chosen along these airway centerlines at intervals varying between 0.3 mm and 1 mm, with the viewing direction chosen parallel to the airway centerline [11]. Virtual images and depth maps were generated by an OpenGL renderer assuming a spot light source at the camera focal point, a field of view of 78.2 degrees and a 264×264 image size to match the calibration parameters of the bronchoscope camera.

Virtual-to-Real Registration

The virtual-to-real registration was performed using pyramid decomposition starting from level 3 and ending at level 1. To account for the difference in intensity characteristics between the imaging sources, the weighted normalized cross-correlation (12) was used as the objective function, with weights $w_{u,v}$ chosen as $$w_{u,v} = 1 - I_v(u,v) \quad (15)$$

in order to emphasize dark areas, which tend to have more information in bronchoscopic video. The video frame, taken from a bronchoscopic procedure performed on h005 was first processed to remove the geometric barrel distortion from the lens to obtain the real image $I_r$. In the virtual-to-real registration case, it is difficult to give ground truth locations as the location of the scope tip is in practice unknown. Without external localization, the quality of a good registration is somewhat qualitative in nature. FIG. 2 shows a sample of the registration results, with edges from the virtual image overlaid on the unregistered and registered real views. The results show that the alignment is qualitatively very satisfying.

Virtual-to-Virtual Registration

In the virtual-to-virtual registration case, the "real" image is actually a rendering generated at a specified location in the airway, but with all depth information discarded. The algorithm uses pyramid decomposition starting from level 3 and ending at level 1, and the weighted SSD objective function was used where the weights $w_{u,v}$ were chosen as in (15) as before.

Figure 3A:
FIGS. 3A-3C show source images and sample results for virtual-to-virtual registration; specifically.
Figure 3B:
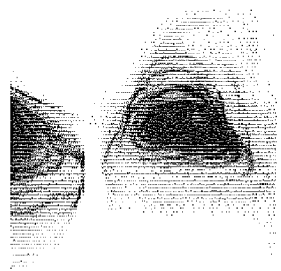
Figure 3C:
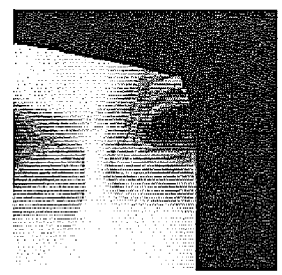
Figure 2A:
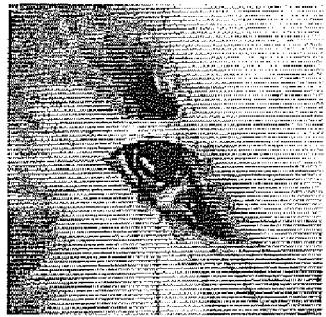
FIGS. 2A-2F show source images and results for virtual-to-real registration; specifically.
Figure 2B:
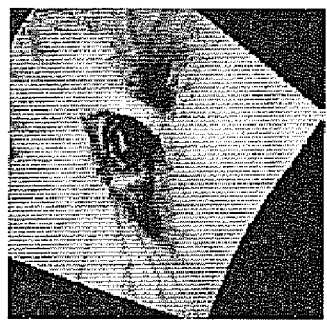
Figure 2C:
Figure 2D:
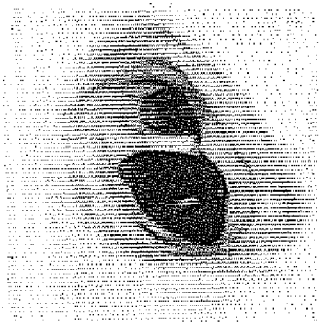
Figure 2E:
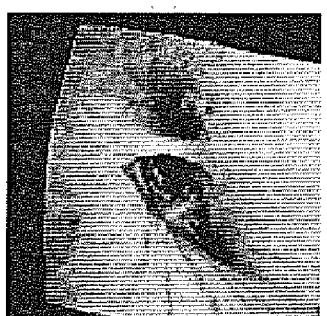
Figure 2F:
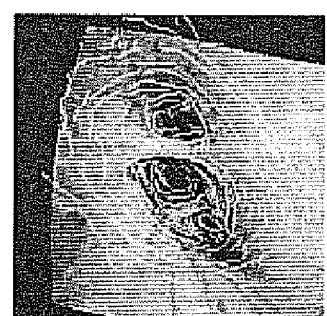

FIG. 3 shows the "real" image $I_r$ prior to registration, the virtual image $I_v$ at the nearest reference site and the warped real image $I_r$ (W(u,v,Z;p)) after registration is complete.

| Viewpoint | X position (mm) | Y position (mm) | Z position (mm) | θα (deg) | θβ (deg) | θγ (deg) |
|---|---|---|---|---|---|---|
| Initial | 147.5 | 149.2 | 71.1 | −20.2 | −1.7 | 0 |
| Reference Site | 146.7 | 149.4 | 73.3 | −7.3 | 5.1 | −19.9 |
| Registered | 147.6 | 149.0 | 73.9 | −20.9 | 1.2 | −3.2 |
| Ground Truth | 147.1 | 148.9 | 73.8 | −20.24 | −1.8 | −0.4 |
| Error | 0.6 | 0.1 | 0.5 | −0.7 | 3.0 | 2.8 |

At least four different alternatives are available for registering the real and virtual sources in the case of bronchoscopy. These scenarios are outlined below:

1. Virtual-to-real registration: real-time or pre-recorded video images $I_r$ from a bronchoscope at an unknown location are registered to a set of endoluminal CT renderings $I_v$ and depth maps $Z_v$.
2. Virtual-to-virtual registration: an endoluminal rendering $I_r$ with unknown location and with or without an associated depth map $Z_r$ is registered to a set of endoluminal CT renderings $I_v$ and depth maps $Z_v$.
3. Real-to-real registration: real-time video images $I_r$ from an endoscope at an unknown location is registered to a set of previously recorded video images $I_v$ with known or estimated depth maps $Z_v$.
4. Real-to-virtual registration: an endoluminal rendering $I_r$ with unknown position and with or without an associated depth map $Z_r$ is registered to a set of previously recorded video images $I_v$ with known or estimated depth maps $Z_v$.

The application has far-reaching applications, particularly in the field of assisted endoscopy. The registration between a CT volume and real-time bronchoscopic video allows the fusion of information between the CT realm and the bronchoscope. This allows regions of interest (ROIs) defined only in the CT volume to be superimposed on the real video frame to assist the physician in navigating to these ROIs. Likewise, airway centerlines, branch labels and metric information such as distances to walls can be displayed on the video frame.

A natural extension of this concept is to other forms of endoscopy such as colonoscopy, where similar guidance information could be displayed on the registered colonoscopic image. Virtual-to-real registration can also be applied to pre-recorded endoscopic video, and opens the door to many post-processing options, such as mapping textural and color information available only in the endoscopic video onto the CT-derived surfaces to enable their visualization from viewpoints not available in the video alone.

An application of the real-to-real registration scenario that can be envisioned for this approach, is for aerial navigation. Satellite imagery, combined with topographic terrain information provides the known 3D environment, while real-time images from a mobile camera aboard an aircraft can be registered to this environment to give the aircraft's location and orientation without GPS or radar information. Similarly, this method also assists in ground-based robotic navigation within a known environment. Reference images and depth maps can be captured at known locations throughout the robot's working environment using a stereo camera setup, and a camera mounted on the robot can be registered to this set of images and depth maps.

REFERENCES

1. H. Minami, Y. Ando, F. Nomura, S. Sakai, and K. Shimokata, "Interbronchoscopist variability in the diagnosis of lung cancer by flexible bronchoscopy," Chest 105(2), pp. 1658-1662, June 1994.
2. I. Bricault, G. Ferretti, and P. Cinquin, "Registration of real and CT-derived virtual bronchoscopic images to assist transbronchial biopsy," IEEE Transactions On Medical Imaging, Vol. 17, No. 5, pp. 703-714, October 1998.
3. J. Helferty, Image-Guided Endoscopy and its Application To Pulmonary Medicine. PhD thesis, The Pennsylvania State University, 2002.
4. D. Deguchi, K. Mori, J. Hasegawa, J. Toriwaki, and H. Natori et al., "Camera motion tracking of real bronchoscope using epipolar geometry analysis and CT derived bronchoscopic images," SPIE Medical Imaging 2002: Physiol. Func. from Multidim. Images A Clough and C. Chen (ed.), v. 4683, pp. 30-41, 2002.
5. B. Lucas and T. Kanade, "An iterative image registration technique with an application to stereo vision," Proceedings of the International Joint Conference on Artificial Intelligence, pp. 674-679, 1981.
6. S. Baker and I. Matthews, "Equivalence and efficiency of image alignment algorithms," Proceedings of the IEEE Conference on Computer Vision and Pattern Recognition 1, pp. 1090-1097, 2001.
7. H.-Y. Shum and R. Szelisld, "*Panoramic Image Mosaics.*" Technical Report MSR-TR-97-23, Microsoft Research.
8. H.-Y. Shum and R. Szeliski, "*Systems and Experiment Paper*: Construction of panoramic image mosaics with global and local alignment," International Journal of Computer Vision 36(2), pp 101-130 (2000).
9. T. Okatani and K. Deguchi, "Shape reconstruction from an endoscope image by shape from shading technique for a point light source at the projection center," Computer Vision and Image Understanding 66, pp. 119-131, May 1997.
10. A. P. Kiraly, E. A. Hoffman, G. McLennan, W. E. Higgins, and J. M. Reinhardt, "3D human airway segmentation for virtual bronchoscopy," SPIE Medical Imaging 2002: Physiology and Funct. from Multidim. Images, A. V. Clough and C. T. Chen, eds. 4683, pp. 16-29, 2002.
11. R. Swift, A. Kiraly, A. Sherbondy, A. L. Austin, E. A. Hoffman, G. McLennan, and W. E. Higgins, "Automatic axes-generation for virtual bronchoscopic assessment of major airway obstructions," Computerized Medical Imaging and Graphics 26, pp. 103-118, March-April 2002.

We claim:

1. A method of registering video frames of a body lumen received from an endoscope inserted into the body lumen to previously acquired images of the body lumen, the method comprising the steps of:
   computing a plurality of reference images of a body lumen, each reference image including a viewpoint with a depth map and image gradients;
   receiving video frames from the endoscope wherein said receiving step comprises receiving a live bronchoscopic video frame associated with an airway; and
   providing a processor to register each video frame received from the endoscope to at least one of the reference images, said processor being programmed to perform the steps of:
   a) warping the video frame to the viewpoint of one reference image of the plurality of reference images or warping one reference image of the plurality of reference images at a viewpoint to the video frame;
   b) automatically computing an image difference between (i) the warped video frame and the reference image, or (ii) the warped reference image and the video frame;
   c) updating a viewpoint of the video frame using an optimization technique; and
   d) repeating steps a) through c) for each video frame until the viewpoint of the video frame converges on a final viewpoint or a next video frame becomes available.

2. The method of claim 1, wherein at least one reference image is updated before, during, or after registration.

3. The method of claim 1, including the step of guessing an initial viewpoint of the video frame.

4. The method of claim 1, wherein the final viewpoint gives an estimate of the relative rotation and translation between the video frame of the video feed and the reference image.

5. The method of claim 1, further including the step of using a resolution pyramid wherein all images, depth maps, and gradients are down-sampled.

6. The method of claim 1, further including the step of using a weighted normalized cross-correlation objective function.

7. The method of claim 1, wherein the optimization technique is based on a Gauss-Newton parameter update.

8. The method of claim 1 wherein the computed set of reference images of a body lumen comprises a 3-D model of a bronchial tree.

9. The method of claim 1 wherein the body lumen is an airway.

10. A method of registering video frames of a body lumen received from an endoscope inserted into the body lumen to previously acquired images of the body lumen, the method comprising the steps of:
    computing a plurality of reference images of a body lumen, each reference image including a viewpoint with a depth map and image gradients;
    receiving at least one video frame from the endoscope; and
    providing a processor to register each video frame received from the endoscope to at least one of the reference images using of the plurality, said processor being programmed to perform the steps of:

a) warping the video frame to the viewpoint of one reference image of the plurality of reference images or warping one reference image of the plurality of reference images at a viewpoint to the video frame;
b) automatically computing an image difference between (i) the warped video frame and the reference image, or (ii) the warped reference image and the video frame;
c) updating a viewpoint of the video frame using an optimization technique; and
d) repeating steps a) through c) for each video frame until the viewpoint of the video frame converges on a final viewpoint or a next video frame becomes available wherein the final viewpoint gives an estimate of relative rotation and translation between the video frame and the reference image.

11. The method of claim 10, wherein at least one reference image is updated before, during, or after registration.

12. The method of claim 10, including the step of guessing an initial viewpoint of the video frame.

13. The method of claim 10, further including the step of using a resolution pyramid wherein all images, depth maps, and gradients are down-sampled.

14. The method of claim 10, further including the step of using a weighted normalized cross-correlation objective function.

15. The method of claim 10 wherein the optimization technique is based on a Gauss-Newton parameter update.

16. The method of claim 10 wherein the step of receiving at least one video frame from an endoscope comprises receiving a live bronchoscopic video frame.

17. The method of claim 16 wherein the computed set of reference images of the body lumen comprises a 3-D model of a bronchial tree.

* * * * *